(12) United States Patent  (10) Patent No.: US 7,500,963 B2
Westbye et al.  (45) Date of Patent: Mar. 10, 2009

(54) SYSTEMS AND METHODS FOR AUTOMATIC MEDICAL INJECTION WITH SAFEGUARD

(75) Inventors: Lars Tommy Westbye, Carlsbad, CA (US); Philip Dowds, San Diego, CA (US)

(73) Assignee: Safety Syringes, Inc., Carlsbad, CA (US)

( * ) Notice: Subject to any disclaimer, the term of this patent is extended or adjusted under 35 U.S.C. 154(b) by 517 days.

(21) Appl. No.: 10/626,218

(22) Filed: Jul. 22, 2003

(65) Prior Publication Data

US 2005/0020979 A1 Jan. 27, 2005

(51) Int. Cl.
*A61M 5/32* (2006.01)
*A61M 5/00* (2006.01)
(52) U.S. Cl. .................. 604/192; 604/110
(58) Field of Classification Search ............ 604/208, 604/192, 134–136, 110, 156, 157, 197, 198, 604/218, 187
See application file for complete search history.

(56) References Cited

U.S. PATENT DOCUMENTS

| 4,022,207 | A |   | 5/1977  | Citrin           |         |
|-----------|---|---|---------|------------------|---------|
| 4,869,249 | A |   | 9/1989  | Crossman et al.  |         |
| 4,923,477 | A |   | 5/1990  | Horvath          |         |
| 5,100,427 | A |   | 3/1992  | Crossman et al.  |         |
| 5,100,428 | A |   | 3/1992  | Mumford          |         |
| 5,104,380 | A | * | 4/1992  | Holman et al.    | 604/117 |
| 5,108,378 | A |   | 4/1992  | Firth et al.     |         |
| 5,242,416 | A |   | 9/1993  | Hutson           |         |
| 5,300,030 | A |   | 4/1994  | Crossman et al.  |         |
| 5,437,647 | A |   | 8/1995  | Firth et al.     |         |
| 5,478,316 | A | * | 12/1995 | Bitdinger et al. | 604/135 |
| 5,501,672 | A |   | 3/1996  | Firth et al.     |         |
| 5,599,309 | A |   | 2/1997  | Marshall et al.  |         |
| 5,611,809 | A |   | 3/1997  | Marshall et al.  |         |
| 5,616,134 | A |   | 4/1997  | Firth et al.     |         |
| 5,624,400 | A |   | 4/1997  | Firth et al.     |         |
| 5,643,214 | A |   | 7/1997  | Marshall et al.  |         |
| 5,928,205 | A |   | 7/1999  | Marshall         |         |
| 6,030,366 | A |   | 2/2000  | Mitchell         |         |
| 6,077,247 | A |   | 6/2000  | Marshall et al.  |         |
| 6,159,181 | A |   | 12/2000 | Crossman et al.  |         |
| 6,159,184 | A |   | 12/2000 | Perez et al.     |         |

(Continued)

FOREIGN PATENT DOCUMENTS

WO   WO 99/37343   7/1999

(Continued)

*Primary Examiner*—Kevin C Sirmons
*Assistant Examiner*—Catherine N Witczak
(74) *Attorney, Agent, or Firm*—Orrick, Herrington & Sutcliffe LLP

(57) ABSTRACT

A medical injection system includes a needle guard and an automatic injection system. The needle guard has a cartridge housing coupled with a release mechanism and configured to house a medical cartridge having a needle, a plunger and a carrier configured to carry the dose. Coupled with the cartridge housing and the release mechanism is a shield that is extendable between a retracted and an extended position that substantially covers the needle. The release mechanism is engageable and configured to maintain the shield in the retracted position and allow the shield to extend upon engagement. The automatic injection system can be configured to house the needle guard and configured to inject the dose when activated.

24 Claims, 9 Drawing Sheets

U.S. PATENT DOCUMENTS

| | | |
|---|---|---|
| 6,171,283 B1 | 1/2001 | Perez et al. |
| 6,203,530 B1 * | 3/2001 | Stewart, Sr. .................. 604/207 |
| 6,230,530 B1 * | 5/2001 | Voigt et al. .................... 70/441 |
| RE37,439 E | 11/2001 | Firth et al. |
| 6,344,032 B1 | 2/2002 | Perez et al. |
| 6,416,323 B1 | 7/2002 | Grenfell et al. |
| 6,425,880 B1 | 7/2002 | Marshall |
| 6,613,022 B1 | 9/2003 | Doyle |
| 6,623,459 B1 | 9/2003 | Doyle |
| 6,805,686 B1 * | 10/2004 | Fathallah et al. ............ 604/135 |
| 2001/0005781 A1 | 6/2001 | Amark |
| 2002/0193746 A1 | 12/2002 | Chevallier |

FOREIGN PATENT DOCUMENTS

| | | |
|---|---|---|
| WO | WO 99/56805 | 11/1999 |
| WO | WO 01/85239 * | 11/2001 |
| WO | WO 03/013632 | 2/2003 |

* cited by examiner

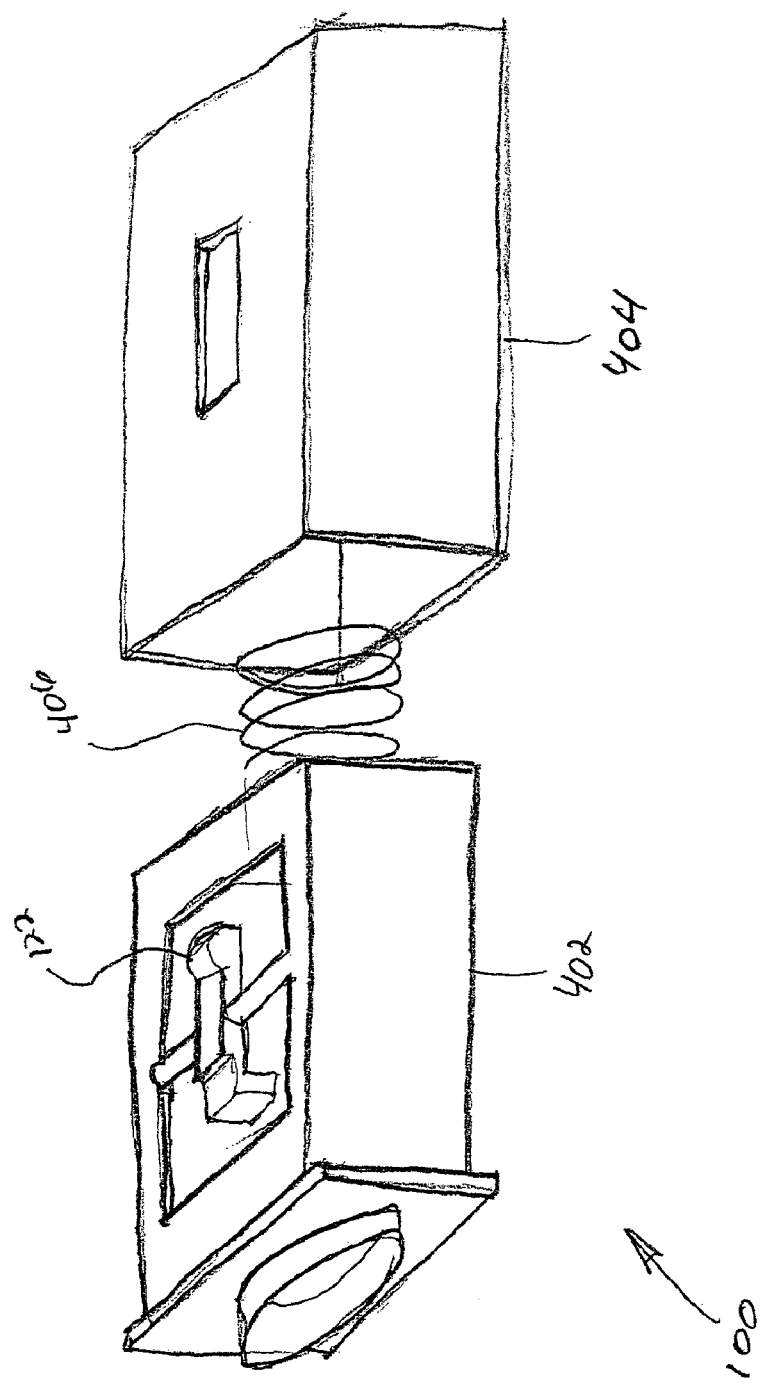

SYSTEMS AND METHODS FOR AUTOMATIC MEDICAL INJECTION WITH SAFEGUARD

FIELD OF THE INVENTION

The field of the invention relates generally to medical injection devices, and more particularly to automatic medical injection devices with a safeguard.

BACKGROUND INFORMATION

Medication is often dispensed using a medical cartridge, such as a syringe, having a carrier, a needle at the distal end of the carrier and a plunger slideably inserted at the proximal end of the carrier. A dose within the carrier is typically a measured volume of a medication, including pharmaceuticals, vaccines, insulin, hormones and any substance which the user desires or needs to inject into himself or a recipient. The dose is delivered through the needle by depressing the plunger distally. Such cartridges are typically referred to as pre-filled syringes and differ from conventional syringes that are furnished empty and are filled by the user before making an injection.

Alternatively, a medical cartridge such as an ampoule or a vial can also be used to dispense a dosage. These cartridges typically include a penetrable seal instead of a needle on one end of the carrier, and/or a piston rather than a plunger on the other end. Such cartridges are generally inserted into an adapter that includes a hollow body to hold the cartridge, a plunger to engage and move the piston in the cartridge, and/or a double-ended needle to penetrate the seal and communicate with the interior of the cartridge.

Many recipients that require various injections use these pre-filled medical cartridges because the medication does not need to be measured out prior to injection. The administration of the injections with medical cartridges is typically neither a desirable nor a safe procedure for recipients. The recipient may be young or does not possess the skill required to safely inject him or herself, or the recipient may have a fear of needles that can render him or her unable to administer the injection. In many cases, the administration of the injection may be in an emergency setting, and the user may not be trained in the injection procedure or may be flustered or rushed into administering the injection incorrectly. Furthermore, the risk of communicable diseases requires a great deal of care when handling a medical cartridge in order to reduce both the risk of an accidental needle stick and the risk of inadvertent needle reuse.

Thus, there is a need for improved medical injection systems and methods of injecting medication.

SUMMARY

An improved medical injection system preferably includes a needle guard and an automatic injection system. Described next is one example embodiment of the medical injection system. In this embodiment, the needle guard preferably includes a cartridge housing coupled with a release mechanism and configured to house a medical cartridge having a needle located on a distal end, a plunger and a carrier configured to carry a dose. Coupled with the cartridge housing and the release mechanism is a shield having an open proximal end and an open distal end. The shield can be configured to extend between a retracted and an extended position that substantially covers the needle when the cartridge is housed in the cartridge housing. The release mechanism is configured to retain the shield in the retracted position and allow the shield to extend upon engagement of the release mechanism. The automatic injection system is preferably configured to house the needle guard and the medical cartridge and configured to deliver the dose when activated. The delivery system can include a drive system configured to depress the plunger and engage the release mechanism when the delivery system is activated, and also an activation system configured to activate the delivery system.

Described next is an example embodiment of an improved method for injecting a dose with the medical injection system. The method preferably includes activating an automatic injection system to inject a dose from a medical cartridge housed within the automatic injection system, wherein activation depresses a plunger extending from the proximal end of the medical cartridge and allows a shield located on a needle guard housing the medical cartridge to extend distally. Then, removing the needle guard from the activation system with the shield in an extended position substantially covering the needle.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

The details of the invention, both as to its structure and operation, may be gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

FIG. 4 is a perspective view of an example embodiment of an unassembled proximal housing within the medical injection system.

DETAILED DESCRIPTION

The systems and methods described herein provide an improved medical injection system having an automatic injection system that automatically injects a dose from a medical cartridge into a recipient and allows removal of that medical cartridge in a safe manner. More specifically, the medical cartridge is housed within a needle guard, and both are, in turn, housed within the automatic injection system.

After the recipient is injected, the needle guard extends over and substantially covers the needle thereby allowing removal of the medical cartridge from the automatic injection system in a safe manner.

Figure 1:
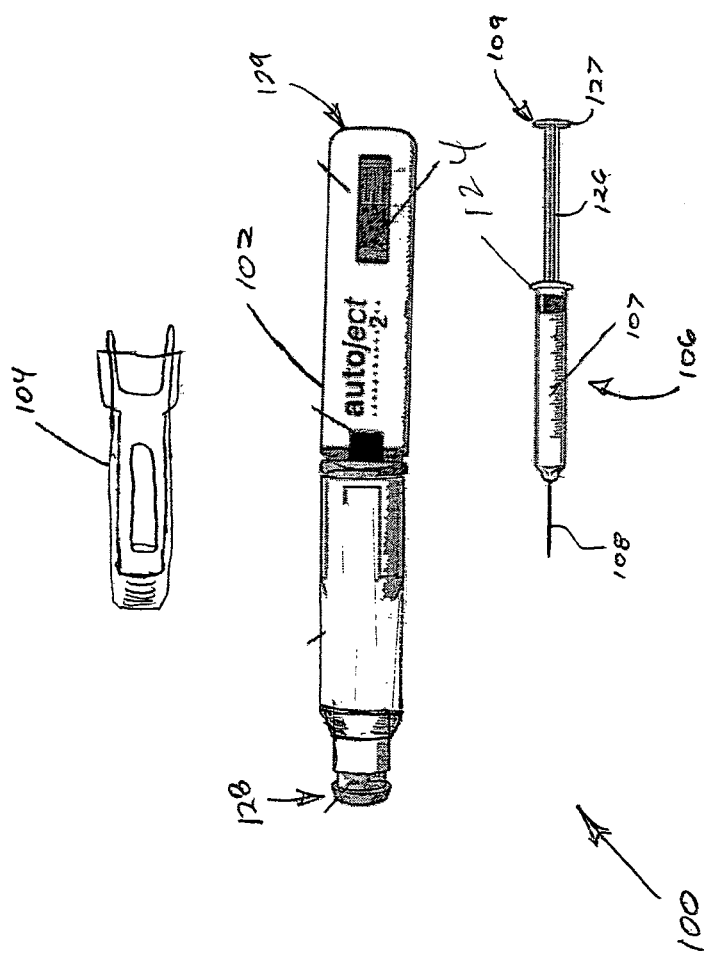
FIG. 1 is a plain view depicting an example embodiment of a medical injection system.

FIG. 1 depicts medical injection system 100, which is a preferred embodiment of the systems and methods described herein. Medical injection system 100 includes automatic injection system 102 and needle guard 104. Needle guard 104 houses medical cartridge 106 and is configured to extend between a retracted position (shown here) and an extended position. Automatic injection system 102 includes distal end 128 and proximal end 129 and is configured to house needle guard 104 and cartridge 106. When activated by a user or recipient, automatic injection system 102 is configured to automatically inject the dose from medical cartridge 106 through distal end 128. Also upon activation, automatic injection system 102 is configured to engage needle guard 104 and allow needle guard 104 to extend. Automatic injection system 102 can be any automatic injection system that facilitates the injection process. In one preferred embodiment, automatic injection system 102 is a modified or customized version of the automatic injection device sold under the name of AUTOJECT2® and manufactured by OWEN MUMFORD, LTD. However, the automatic injection system 102 is not limited to solely modified or customized versions of the AUTOJECT2® and its variants, and can include any automatic injection system 102, which can automatically inject a dose into a recipient.

After the dose is injected, needle guard 104 extends to the extended position substantially covering needle 108. The extended needle guard 104 allows medical cartridge 106 to be removed from automatic injection system 102 in a safe manner. More specifically, a user can remove and handle the used medical cartridge 106 with a reduced risk of inadvertent needle penetration, e.g., a "needle stick," in addition to being deterred or prevented from reusing medical cartridge 106 on a different recipient.

Medical cartridge 106 can be any device configured to inject a dose, such as a medical cartridge, a syringe and the like. In this embodiment, medical cartridge 106 includes carrier 107 with needle 108 and plunger 109 located on the distal and proximal ends of cartridge 106, respectively. Carrier 107 carries the dose, which is delivered through needle 108 by the depression of plunger 109. Plunger 109 preferably includes shaft 126 and contact portion 127, which can be an enlarged portion located at the proximal end of shaft 126 and configured to facilitate the depression of plunger 109. In one embodiment, contact portion 127 is larger than a typical contact portion in order to facilitate engagement of needle guard 104. Cartridge 106 can optionally include a flange 124 at the proximal end of carrier 107 for engaging with needle guard 104. It should be noted that the design and configuration of cartridge 106 will vary between applications and embodiments, and one of skill in the art will readily recognize that the implementation of system 100 is flexible, and accordingly system 100 can be configured to function with all embodiments of cartridge 106.

Figure 2:
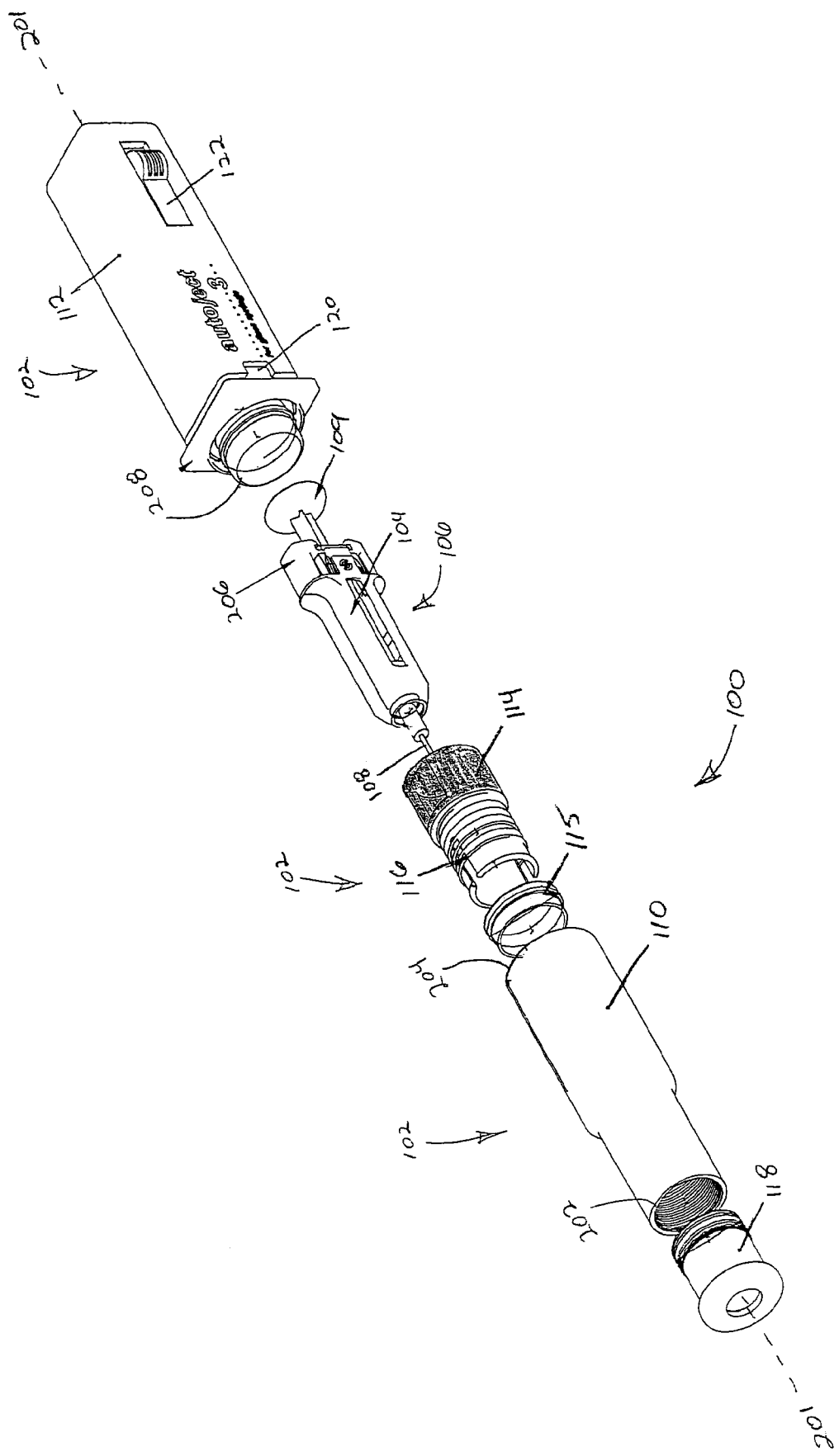
FIG. 2 is a perspective view of another example embodiment of an unassembled medical injection system.

FIG. 2 depicts an expanded perspective of a preferred embodiment of medical injection system 100 in the order in which the various elements of system 100 are preferably assembled. Here, automatic injection system 102 includes distal housing 110, proximal housing 112, sleeve 114, ring 115, sleeve bias member 116, depth adjuster 118, indicator 120 and activation system 122. Distal housing 110 has open distal end 202 and open proximal end 204. Distal end 202 is preferably configured to allow needle 108 to pass through and into a user in order to administer the injection.

Distal end 202 is also configured to couple with depth adjuster 118, which is configured to set the depth of penetration of needle 108. Depth adjuster 118 can be extendable from the distal end 202 and fixable in a desired extended position. In this embodiment, depth adjuster 118 is threadably coupled to distal housing 110 and includes an index configured to identify the depth of penetration of needle 108. To achieve a greater penetration depth, adjuster 118 is screwed further into housing 110 and the converse is also applicable for a lesser penetration depth. Activation system 122 is configured to activate automatic injection system 102.

In this embodiment, sleeve 114, ring 115 and sleeve bias member 116 are mostly housed within distal housing 110 and sleeve 114 is configured to slide axially within automatic injection system 102 along center axis 201. Sleeve 114 can be slideably coupled with ring 115 and configured to receive needle guard 104, preferably in a manner that maintains the orientation of needle guard 104 throughout the entire range of axial slide motion of sleeve 114. Maintaining the orientation of needle guard 104 increases the likelihood that needle 108 will enter the user at an angle substantially parallel to the center axis 201. Sleeve 114 preferably includes a detent or other surface that abuts needle guard 104 and prevents movement of needle guard 104 distally within sleeve 114. In one embodiment, needle guard 104 includes raised portion 206, which abuts sleeve 114. Ring 115 can be coupled with distal housing 110, preferably on the inner surface of distal housing 110, and can be configured to anchor sleeve 114 and set the distal and proximal limits to the motion of sleeve 114. In one alternative embodiment, the functionality provided by ring 115 is integrated directly into distal housing 110, i.e., distal housing 110 is configured to couple directly with sleeve 114.

Sleeve bias member 116 can be concentrically disposed between sleeve 114 and ring 115. Sleeve bias member 116 applies pressure to sleeve 114 in a proximal direction and maintains sleeve 114 in a proximal position within distal housing 110 prior to injection. Sleeve bias member 116 can be any system or device which can apply pressure or bias, either non-linear or linear, such as a spring, hydraulic, compressible material and the like. Sleeve bias member 116 can also be compressible and can cushion any distal movement of needle guard 104 within the system 102 during an injection procedure, prior to depression of plunger 109.

In a preferred embodiment, sleeve 114 guides the axial motion of needle guard 104 and medical cartridge 106 within automatic injection system 102. Sleeve 114 can be configured to slide between a distal position where needle 108 is exposed from injection system 102, and a proximal position where needle 108 is substantially unexposed. The proximal and distal limits to this range of slide motion can be determined in any manner. For instance, sleeve 114 and ring 115 can include cooperating detents or opposing surfaces to interact and limit the range of motion. The range can also be determined by the limits to compression or expansion of sleeve bias member 116 or by the interaction of sleeve 114 with other elements of system 100. It should be noted that these are merely examples and that the limits can be modified according to the needs and design of each application.

Proximal housing 112 is attachable to distal housing 110 in any manner in accordance with the needs of the application, including, but not limited to the use of a screw, snap, latch, fastener and the like. Here, proximal end 204 of distal housing 110 is threadably attachable to open distal end 208 of proximal housing 112. Preferably, needle guard 104, in the retracted position and housing a loaded medical cartridge 106, is placed into sleeve 114 before attaching distal and proximal housings 110 and 112. Prior to injection, needle guard 104 is preferably kept in the proximal position within system 102 by the pressure applied by sleeve bias member 116.

As mentioned above, in a preferred embodiment, automatic injection system 102 is a modified version of a standard AUTOJECT2® device. In this embodiment, AUTOJECT2® device 102 is modified to allow needle guard 104 to fit and operate within. Because plunger 109 can be larger than a typical plunger in order to facilitate engagement of needle guard 104, open distal end 208 of proximal housing 112 can be enlarged to allow plunger 109 to pass into proximal housing 112. In most embodiments, needle guard 104 is wider than a typical medical cartridge 106, in which case distal housing 110, sleeve 114 ring 115 and/or sleeve bias member 116 can be enlarged to receive the wider needle guard 104.

Preferably, sleeve 114 and distal housing 110 both surround the circumference of needle guard 104 to reduce the likelihood of needle guard 104 becoming obstructed when moving within system 102. However, in one embodiment, a portion of the walls of sleeve 114 can be removed to allow raised portion 206 of needle guard 104 to fit within without substantially enlarging sleeve 114. Also, needle guard 104 can have numerous body shapes and, accordingly, sleeve 114 can be configured to receive any body shape configuration of needle guard 104. It should be noted that this is not an exhaustive list of modifications to AUTOJECT2® device 102 and more modifications and customizations will be discussed herein. Also, one of skill in the art will recognize that additional modifications can be made to satisfy the needs of the particular application.

Figure 3A:
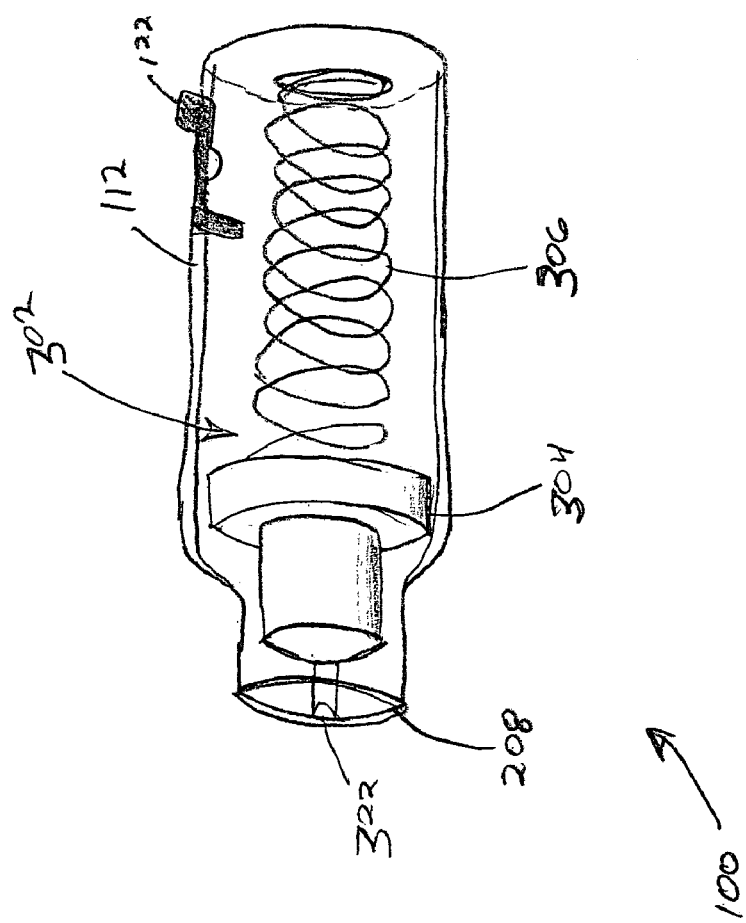
FIG. 3A is a perspective view of an example embodiment of a drive system within the medical injection system.
Figure 3B:
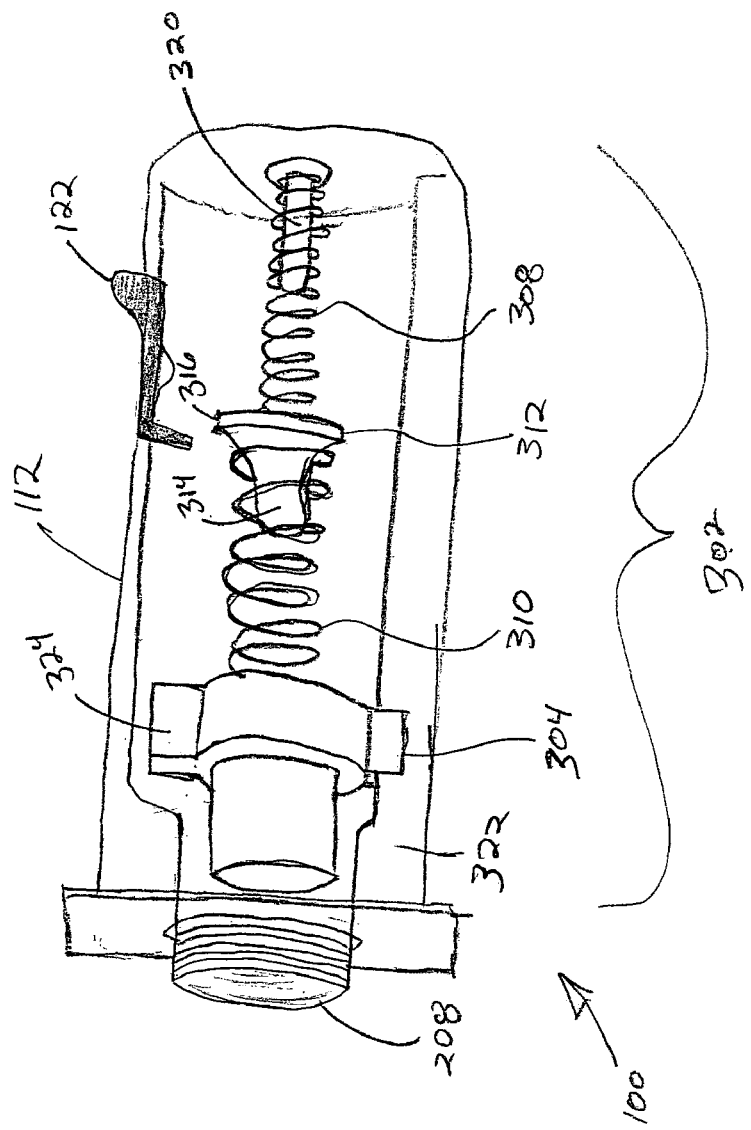
FIG. 3B is a perspective view of another example embodiment of a drive system within the medical injection system.
Figure 5:
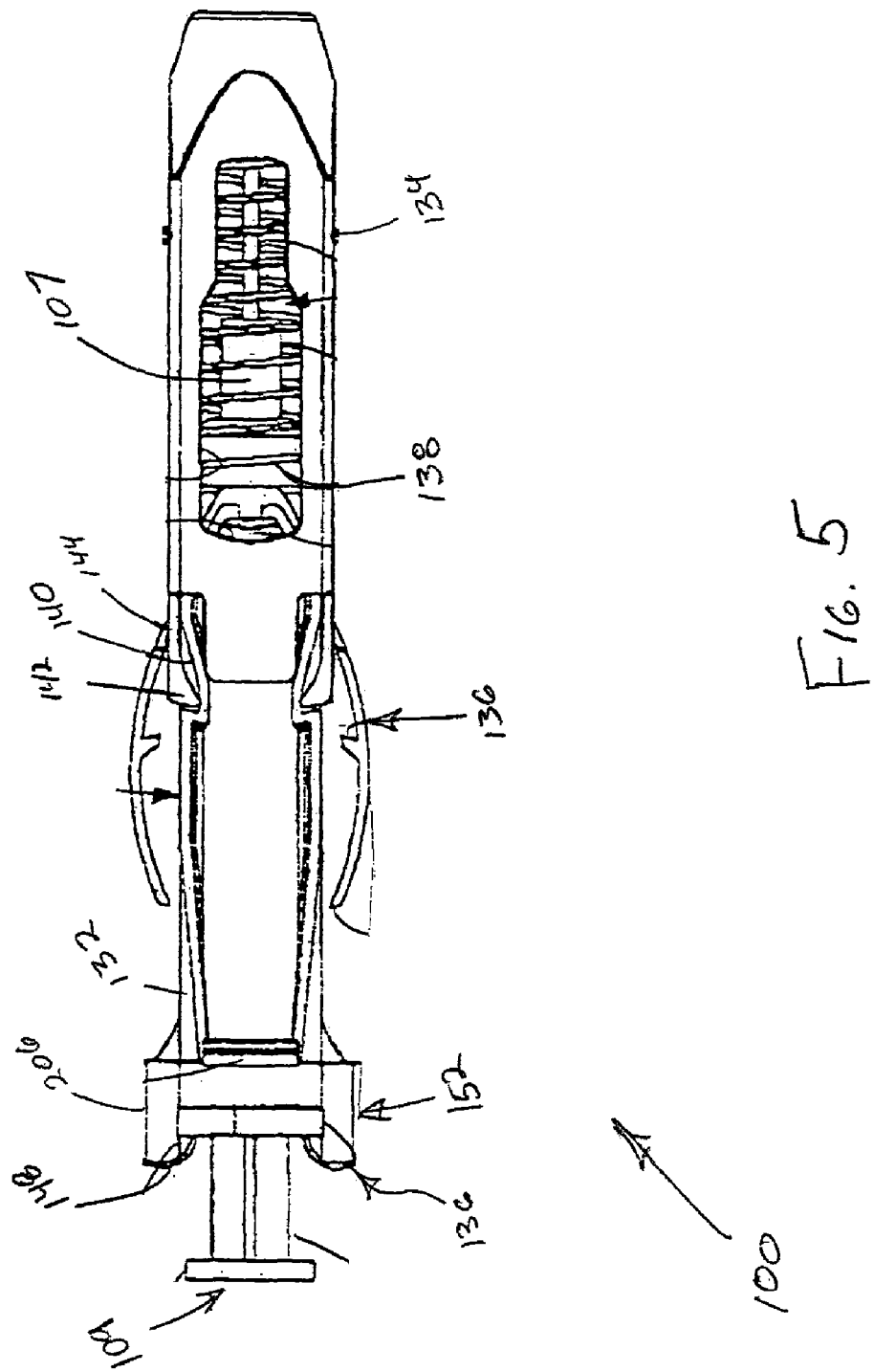
FIG. 5 is a plain view of an example embodiment of a needle guard within the medical injection system.
Figure 7:
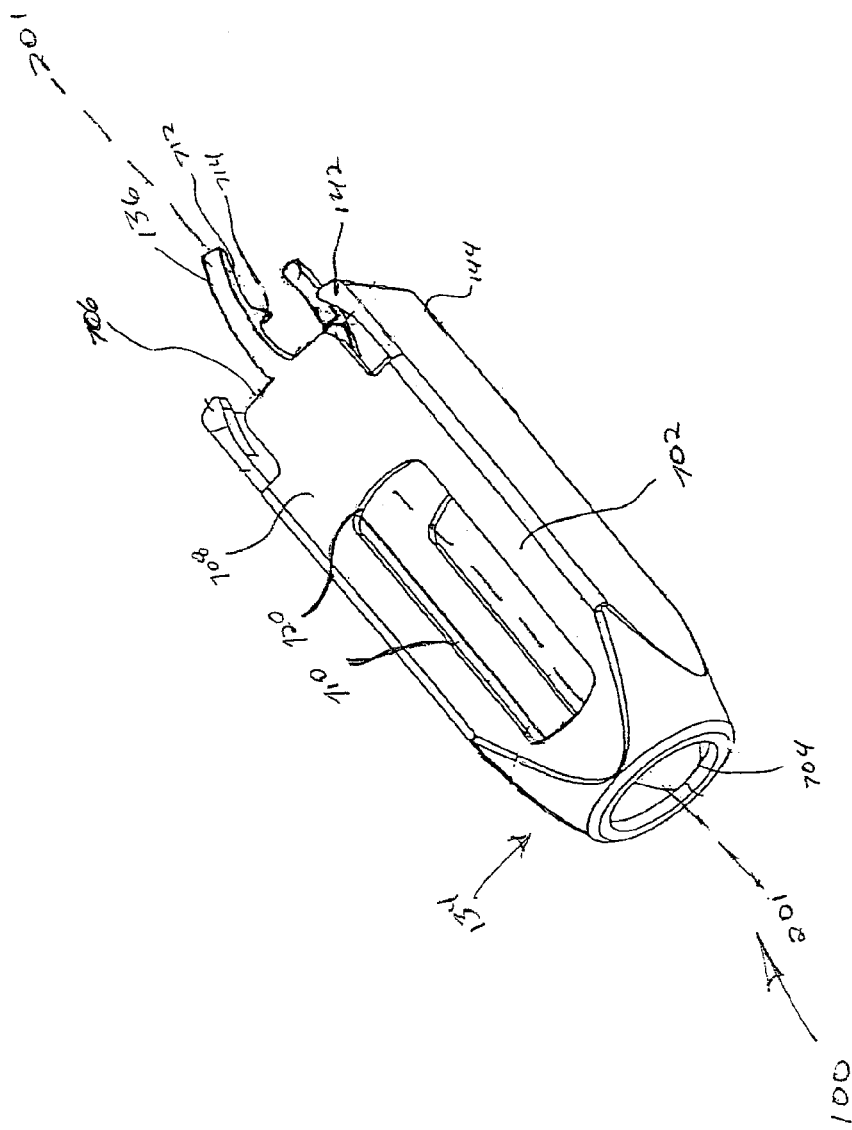
FIG. 7 is a perspective view of an example embodiment of a shield within the medical injection system.

Preferably, automatic injection system 102 houses drive system 302, which is depicted in FIGS. 3A-B. FIG. 3A depicts one embodiment of drive system 302, including driver 304 and drive bias member 306. Drive system 302 can be coupled with proximal housing 112 and configured to depress plunger 109 when automatic injection system 102 is activated. System 100 can be configured so that the depression of plunger 109 engages a release mechanism 136 (not shown here), which allows needle guard 104 to extend to the extended position. Release mechanism 136 is depicted in FIGS. 5 and 7 and discussed in more detail below. Driver 304 can be configured to contact the proximal end of plunger 109 and is preferably coupled with drive bias member 306. Drive bias member 306, in turn, can be coupled or placed into contact with proximal housing 112 and configured to apply pressure to driver 304 in a distal direction. This pressure is preferably sufficient to compress sleeve bias member 116, insert needle 108 into the recipient and depress plunger 109. Drive bias member 306 can be any system or device which can apply pressure or bias, either non-linear or linear, such as a spring, hydraulic, compressible material and the like.

Driver 304 is axially translatable, or movable, within automatic injection system 102, between a retracted and extended position. Preferably, drive system 302 is releasably coupled with activation system 122, which can be configured to maintain driver 304 in the retracted position until activation, at which point driver 304 can be released to depress plunger 109. In the embodiment depicted in FIG. 2, activation system 122 is a depressible button housed in proximal housing 112. It should be noted that any activation system can be used in system 100, including, but not limited to a button, latch, lever, switch and the like or any electrical or mechanical means or combination thereof.

Preferably, driver 304 is placed in the retracted position prior to attachment of the distal and proximal housings 110 and 112. The retracted position is a proximal position where drive bias member 306 can apply pressure to driver 304 upon release and move driver 304 distally within system 102 along axis 201. Upon release, drive bias member 306 moves driver 304 from the retracted to the extended position. The location of the extended position can be dependent on the design and configuration of system 102 or the needs of the application. For instance, the extended position can be the distal limit to motion of driver 304, set by stop mechanism 324, which is discussed in more detail below. The extended position can also be the limit to movement once plunger 109 is depressed and sleeve 114 (if included) is at the distal limit of movement.

Driver 304 can be in contact with plunger 109 when system 100 is assembled and loaded, i.e., when housings 110 and 112 are attached with the loaded medical cartridge 106 and needle guard 104 within. In one example embodiment, after system 100 is assembled and loaded, needle guard 104 and cartridge 106, with plunger 109 fully extended, are held snugly in place. Preferably, sleeve bias member 116 applies pressure to maintain the proximal end of plunger 109 in contact with driver 304, thereby limiting the movement of guard 104 and cartridge 106 while within system 102. Maintaining plunger 109 in contact with driver 304 can facilitate the injection process by limiting the impact on cartridge 106 once release occurs. Preferably, enough room is left within system 102 so that needle 108 remains unexposed and sleeve bias member 116 is partially compressed and still capable of providing adequate cushioning to needle guard 104 and cartridge 106.

FIG. 3B depicts another embodiment of drive system 302, including driver 304, inner drive bias member 308 and outer drive bias member 310. Inner and outer bias members 308 and 310 can be any system or device which can apply pressure or bias, either non-linear or linear, such as a spring, hydraulic, compressible material and the like. In this embodiment, drive bias members 308 and 310 are cylindrical springs. Outer drive bias member 310 preferably has a diameter greater than the diameter of the inner bias member 308 such that inner bias member 308 can be compressed and expanded within outer bias member 310. Drive system 302 also includes coupling 312 configured to abut a proximal end of outer bias member 310 and a distal end of the inner bias member 308. Coupling 312 couples both bias members 308 and 310 together while within system 102 and allows both bias members 308 and 310 to cooperatively extend and compress.

In one embodiment, coupling 312 includes hollow cup portion 314 and flange 316. Preferably, cup portion 314 has a diameter less than outer bias member 310 such that outer bias member 310 can slide over cup portion 314 and abut flange 316. The diameter of the inside of hollow cup 314 is preferably greater than the diameter of inner bias member 308, so that cup 314 can receive and abut inner bias member 308. Drive system 302 can optionally include guide 320 for maintaining the orientation of inner bias member 308 and guiding the compression and expansion of the bias members 308 and 310. By cooperatively coupling multiple bias members, this embodiment can increase the pressure appliable by drive system 302 and also provide for non-linear spring compression and expansion.

Proximal housing 312 can include guide 322 for guiding the axial motion of driver 304 within system 102. Guide 322 can be located on an inner surface of proximal housing 112. Proximal housing 112 also can include stop mechanism 324 for stopping driver 304 from extending outside of proximal housing 112, or from extending distally from housing 112 past a predetermined distance. The predetermined distance can be any distance in accordance with the needs of the application. For instance, in one embodiment the predetermined distance is a distance sufficient to allow full depression of plunger 109. Here, the stop mechanism is flange 324 on driver 304 that abuts the distal end of proximal housing 112. However, one of skill in the art will readily recognize that numerous different embodiments of stop mechanism 324 exist and accordingly, system 100 is not limited to any one embodiment.

Referring back to FIG. 2, depicted therein is indicator 120, which can be optionally included in system 100. Preferably, indicator 120 indicates completion of the injection once the dose is injected. In one embodiment, indicator 120 is a colored surface located on driver 304 and is viewable through an opening on proximal housing 112. Once driver 304 is extended such that plunger 109 is substantially depressed, the colored portion of indicator 120 is viewable through the opening and indicates completion of the injection procedure.

FIG. 4 depicts another embodiment of system 100 where proximal housing 112 includes inner proximal housing 402 slideably coupled with an outer proximal housing 404. In this embodiment, outer proximal housing 404 is configured to slide over inner proximal housing 402 between an extended position and a retracted position. Housing bias member 406 is preferably located between inner housing 402 and outer housing 404 and can be configured to apply pressure between the two housings 402 and 404 and maintain housing 404 in the extended position. Housing bias member 406 can be any system or device which can apply pressure or bias, either non-linear or linear, such as a spring, hydraulic, compressible material and the like.

In this embodiment, activation system 122 is configured to activate when outer housing 404 is in the retracted position. For instance, in operation the user can apply pressure to outer housing 404 in a distal direction, overcoming the pressure applied by housing bias member 406 and sliding outer housing 404 into the retracted position where activation system 122 can be activated. In this manner, the risk of accidental activation of automatic injection system 102 is lessened. Because numerous embodiments of activation system 122 exist, the manner of allowing activation can vary. In this embodiment, depressible button 122 depresses like a lever, and is housed in inner proximal housing 402. In order to depress button 122, the lever motion is preferably unrestricted, and this embodiment is configured so that this motion is unrestricted when outer housing 404 is in the retracted position.

To use system 100 to administer an injection, the user preferably places distal end 128 of system 100 in the position where the injection is to be administered and then activates activation system 122. Activation of system 122 allows driver 304 to extend and apply pressure distally to plunger 109. This pressure is preferably greater than the pressure applied by sleeve bias member 116 and causes needle guard 104 and cartridge 106 to move axially in a distal direction within system 102, thereby exposing needle 108 from the distal end of system 102. Drive system 302 continues to apply pressure until sleeve 114 stops distal movement, at which point the pressure causes plunger 109 to depress.

Preferably, drive system 302 is configured to depress plunger 109 until the dose is substantially injected. In some embodiments there may be a residual amount of the dose that is remaining in medical cartridge 106 but does not have a significant impact on the recipient. The depression of plunger 109 engages release mechanism 136 and enables needle guard 104 to extend to the extended position, which can occur within system 102 or once distal and proximal housings 110 and 112 are detached. Once extended, needle guard 104 substantially covers needle 108 and reduces the risk of a needle stick and the like.

FIG. 5 depicts one preferred embodiment of needle guard 104 in an extended position. Needle guard 104 includes cartridge housing 132 and shield 134, which can be coupled together. Cartridge housing 132 is configured to house medical cartridge 106. Shield 134 is preferably slideably coupled to housing 132 and extendable between the retracted position and the extended position where it substantially covers needle 108. Automatic injection system 102, when driver 304 is in the retracted position, is preferably configured to house needle guard 104 with shield 134 in the retracted position and plunger 109 fully extended. Cartridge housing 132 and shield 134 are both coupled with release mechanism 136. Release mechanism 136 is configured to maintain shield 134 in the retracted position, and to allow shield 134 to extend to the extended position once release mechanism 136 is engaged. Release mechanism 136 also preferably allows shield 134 to extend while plunger 109 remains exposed from proximal end 152 of housing 132 such that plunger 109 can be fully depressed and substantially the entire dose can be injected.

In one embodiment, release mechanism 136 can be formed in both housing 134 and shield 136, however, mechanism 136 can also be a discrete component coupled with housing 132, shield 134 or both. In one embodiment, the depression of plunger 109 engages release mechanism 136 and causes it to release shield 134 from housing 132. Release mechanism 136 can be engaged in any manner, either with the depression of plunger 109 or by any separate means either activated by activation system 122 or activated separately. For instance, release mechanism 136 could also be engaged when housings 110 and 112 are attached, or by a separate activation system and so forth.

Shield bias member 138 preferably contacts both housing 132 and shield 134 and is configured to apply pressure to shield 134 to extend shield 134 to the extended position. In one preferred embodiment, shield bias member 138 is a spring concentrically disposed within shield 134. Shield bias member 138 can be any system or device which can apply pressure or bias, either non-linear or linear, such as a spring, hydraulic, compressible material and the like.

Needle guard 104, or shield 134, can also be configured to lock in the extended position to provide additional protection against exposure of needle 108. Any locking device or mechanism can be used in accordance with the needs of the application, such as cooperating detents, latches, snaps, levers, structures collapsible upon extension and the like. Here, housing 132 and shield 134 include cooperating detents 140 and 142, respectively. In this embodiment, cooperating detents 142 are coupled with shield 134 by flexible arm 144. Detents 142 are inwardly disposed to engage with cooperating detents 140. Flexible arm 144 is biased such that as shield 134 extends over needle 108, arm 144 moves inwardly to engage cooperating detent 142 and lock shield 134 in the extended position.

One of skill in the art will readily recognize that, while needle guard 104 is substantially locked in the extended position, manipulation of cooperating detents 140 or 142 can unlock needle guard 104. The level of manipulation required to unlock needle guard 104 is dependent on the needs of the application. For instance, in applications where there is a risk of a minor handling needle guard 104, it can be desirable to implement detents 140 and 142 and arm 144 in a manner that requires relatively more manipulation to unlock needle guard 104.

Figure 6:
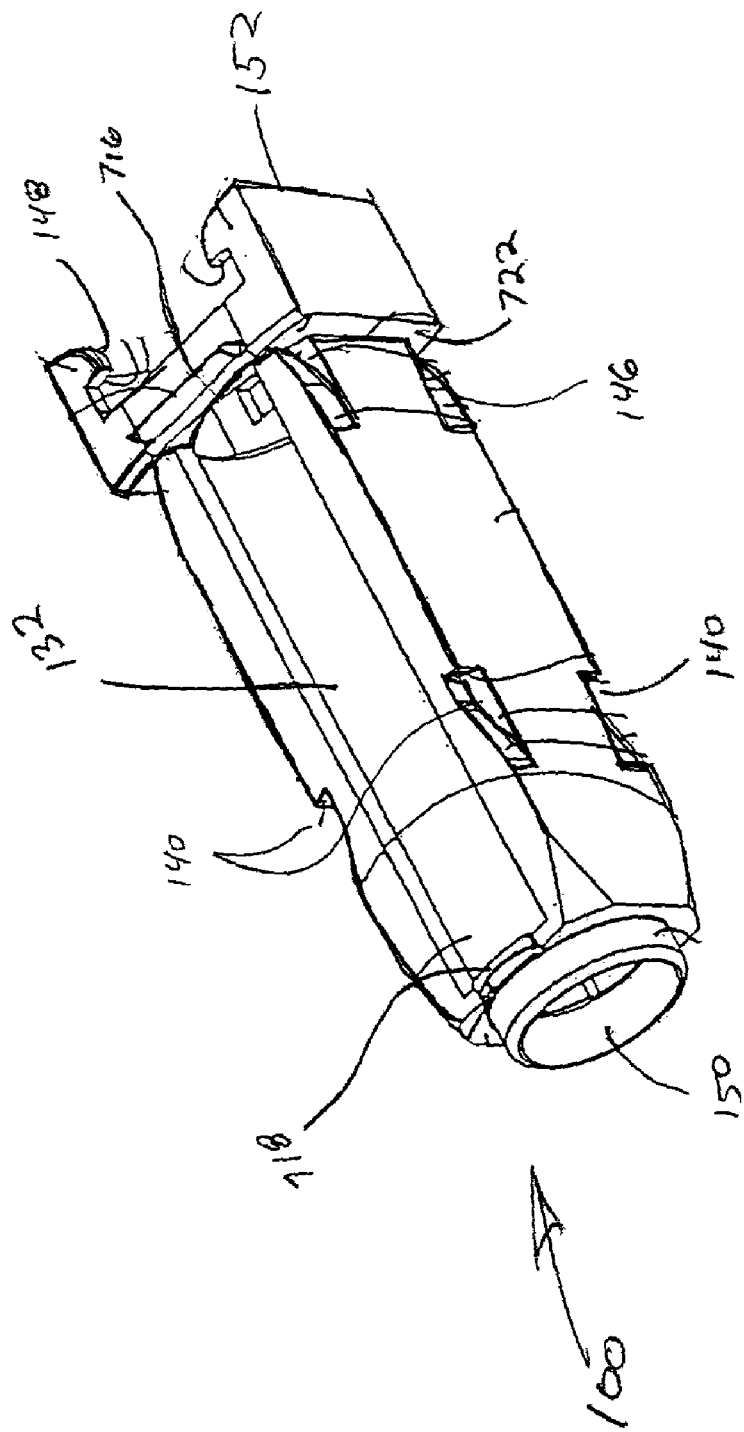
FIG. 6 is a perspective view of an example embodiment of a cartridge housing within the medical injection system.

FIG. 6 is a perspective view of one embodiment of cartridge housing 132, showing cooperating detents 140 and 146, retainment device 148 and open distal and proximal ends 150 and 152, respectively. Medical cartridge 106 is preferably insertable into cartridge housing 132 such that needle 108 can extend from distal end 150 and plunger 109 can extend from proximal end 152 and carrier 107 is housed therebetween. Cooperating detents 146 engage with cooperating detents 142 when shield 134 is in the retracted position and help retain shield 134. Detents 146 preferably allow shield 134 to slide to the extended position with minimal resistance. As shield 134 extends, flexible arms 144 deflect outwardly until they engage detents 142. In this embodiment, arms 144 have a predisposition to remain in the inward position. The flexibility in arms 144 is provided by the flexibility of the material used to fabricate shield 134. Detents 146 facilitate the retention of this predisposition by allowing arms 144 to maintain in the inward position.

Retainment device 148 is configured to retain cartridge 106 within housing 132 during the injection procedure. In this embodiment, retainment device 148 is located at proximal end 152 and engages with the proximal end of cartridge 106. Retainment device 148 preferably retains, or secures, cartridge 106 within housing 132. Retainment device 148 can be configured as a deflectable latch (shown here) that deflects as carrier 107 is inserted, and then returns and engages the proximal end of carrier 107. As mentioned previously, carrier 107 can include flange 124 to facilitate engagement with retainment device 148. Housing 132 can include one or more retainment devices 148, the actual number being dependent on the needs of the application. Furthermore, retainment device 148 can be any device that retains or secures cartridge 106 within housing 132, including a latch, hook, snap, lever and the like. Retainment device 148 can also be deflectable outwards to allow the disengagement and removal of cartridge 106, however, it should be noted that removal of cartridge 106 increases the risk of inadvertent needle penetration after injection.

FIG. 7 depicts one preferred embodiment of shield 134. Shield 134 includes rigid body 702 and open distal and proximal ends 704 and 706, respectively. In this embodiment, open distal end 704 is configured to expose needle 108 for injection when shield 134 is in the retracted position. Open proximal end 706 is configured to allow shield 134 to slide over housing 132. Rigid body 702 is substantially rigid so as to lower the risk of penetration of rigid body 702 to a safe level determined by the needs of the individual application. Rigid body 702 can also be resistant to any various impacts, pressures and stresses that could be placed on shield 134 during normal use. Factors affecting the necessary level of rigidity of shield 134 will depend on the individual application. Some examples of materials from which shield 134 can be fabricated include plastic, metal, glass, ceramic, rubber and the like.

Shield 134 is also configured to substantially cover needle 108 while in the extended position. Needle 108 is substantially covered when the risk of exposure is reduced to a level adequate for the needs of the individual application. For instance, in one preferred embodiment, distal end 704 is open but the opening is not large enough to allow unforced contact with human skin tissue. Also, in one embodiment, sides 708 of shield 134 have guides 710 which also are not large enough to allow the contact with needle 108. Any openings in shield 134 should take into account the needs of the application. For instance, in some applications, there may be a risk of a child inserting a finger through an opening in shield 134 and contacting needle 108, while in other applications only the risk of exposure to an adult finger may be significant. These are merely examples of the factors that can be taken into account in the implementation of shield 134 and do not comprise an exhaustive list.

In this embodiment, release mechanism 136 includes latch member 712 and cooperating catches 714 and 716. Cooperating catch 714 is inwardly disposed and located on latch member 712, which extends proximally from proximal end 706 of shield 134. Catch 714 is configured to engage cooperating catch 716 on housing 132 when shield 134 is in the retracted position. The engagement of catches 714 and 716 maintains shield 134 in the retracted position. Cooperating catches 714 and 716 are further configured to disengage when release mechanism 136 is engaged while shield 134 is in the retracted position. Latch member 712 is preferably deflectable upon depression of plunger 109.

In a preferred embodiment, the depression of plunger 109 causes contact portion 127 to contact the proximal end of latch member 712. The continued depression of contact portion 127 causes latch member 712 to deflect outwards thereby disengaging catch 714 from catch 716. Once catches 714 and 716 are disengaged, shield 134 is released and allowed to extend through the pressure applied by shield bias member 138. Shield 134 extends until flange 718 (located on cartridge housing 132 and depicted in FIG. 6) contacts abutment 720, located on the proximal end of guide 710. The design and configuration of release mechanism 136 can be implemented in numerous different embodiments, as one of skill in the art will readily recognize. For instance, latch member 712 can also be configured to extend proximally from cartridge housing 132 and so forth.

Flange 718 can be configured to extend into guide 710, which, in this embodiment, is an opening configured to guide the extension of shield 134 in relation to housing 132. More specifically, guide 710 guides shield 134 and prevents shield 134 from twisting radially around center axis 201 or deflecting in a direction perpendicular to center axis 201 while shield 134 extends. Abutment 720 of guide 710 contacts flange 718 and prevents shield 134 from moving any further in a distal direction. Abutment 720 is located such that the distal limit to movement of shield 134 allows cooperating catches 140 and 142 to engage. In this manner, shield 134 is locked in the extended position and the likelihood of movement of shield 134 is significantly lessened. One of skill in the art will recognize that the manipulation of catches 142 or the use of excessive force beyond that reasonably anticipated by the individual application can cause shield 134 to be unlocked. The actual design and implementation of system 100 is dependent on the needs of each individual application to guard against the unwarranted unlocking of shield 134. Accordingly, additional safeguards can be implemented as needed.

In this embodiment, cooperating catches 714 are preferably located at a height on latch member 712 that allows catches 714 to catch catches 716 and maintain shield 134 in the retracted position, preferably without allowing excessive movement of shield 134 in a proximal direction. In one embodiment, when catches 714 and 716 are engaged, shield bias member 138 is fully compressed, thereby limiting the proximal movement of shield 134. In another embodiment, when catches 714 and 716 are engaged, the proximal end of shield 134 abuts abutment 722 on housing 132. Excessive movement of shield 134 while in the retracted position, increases the risk that catches 714 and 716 will disengage prematurely. One of skill in the art will readily recognize numerous other methods systems for limiting the proximal movement of shield 134 while in the retracted position.

The distance that latch member 712 extends proximally from shield 134 can determine the point at which the depression of plunger 109 engages release mechanism 136. In a preferred embodiment, this distance is configured to cause contact portion 127 to engage release mechanism 136 once the dose is substantially delivered, i.e., plunger 109 is substantially fully depressed. This distance is determined by the needs of the application. In other embodiments, it may be desired for release mechanism 136 to be engaged as soon as depression of plunger 109 begins, in which case the distance by which latch member 712 extends would be increased. This can provide protection by allowing shield 134 to extend in the instance that only a partial dose is delivered by automatic injection system 102.

Because automatic injection system 102 can be used in handheld applications, it may be desirable to limit the overall width of system 102. Accordingly, in these embodiments needle guard 104 is configured to fit within system 102. In one embodiment, needle guard 104 is fingergrip-less and does not include an outwardly extending finger grip. Such fingergrips are typically included in applications where needle guard 104 is used without the aid of automatic injection system 102. In these applications, the fingergrip is used to gain leverage and counteract the pressure applied to depress plunger 109. However, needle guard 104, including cartridge housing 132 and shield 134, can be fingergrip-less in order to reduce the width of needle guard 104 and facilitate movement within automatic injection system 102. The elimination of one or more fingergrips can also include the elimination of any substantial outcropping extending from needle guard 104 that could be used as a fingergrip.

Figure 8:
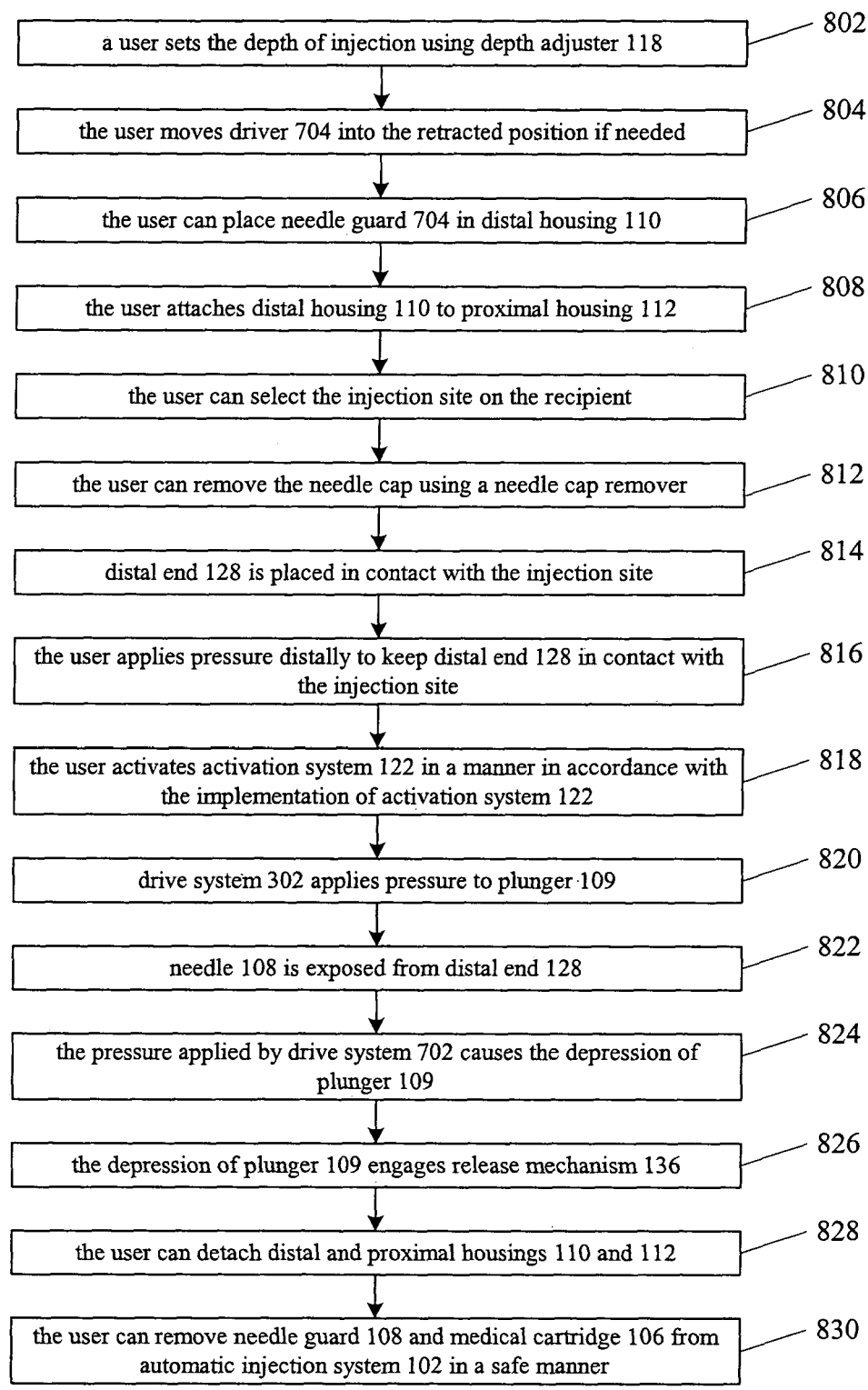
FIG. 8 is a flow diagram of an example embodiment of a method of injecting a dose with the medical injection system.

FIG. 8 depicts a preferred embodiment of method 800 of injecting a dose from medical cartridge 106 while housed with needle guard 104 and automatic injection system 102. Initially, at 802, a user sets the depth of injection using depth adjuster 118. If depth adjuster 118 is threadably attached to distal housing 110, the user screws the depth adjuster into distal housing 110 to increase the depth of penetration and vice-versa. Next, at 804, the user moves driver 304 into the retracted position if needed. This is preferably done using distal end 128 of distal housing 110, which can be configured to interface with, or fit in or over driver 304 to facilitate the positioning of driver 304 in the retracted position. Preferably, once driver 304 is in the retracted position, activation system 122 releasably couples with driver 304 and maintains driver 304 in the retracted position.

At 806, the user can place needle guard 104 in distal housing 110. Needle guard 104 is preferably supplied to the user pre-assembled with medical cartridge 106 already housed within. However, medical cartridge 106 can be inserted into needle guard 104 and engaged with retainment device 148 by the user if needed. In an embodiment where distal housing 110 includes sleeve 114, needle guard 104 is preferably placed into sleeve 114 so that needle guard is received and held in position by sleeve 114. At 808, the user attaches distal housing 110 to proximal housing 112. If distal and proximal housings 110 and 112 are threadably attachable, the user screws the two housings together. Preferably, once attached, driver 304 is placed in contact with contact portion 127 of plunger 109 in order to reduce the shock to cartridge 106 once driver 304 is released. At this point, needle 108 is preferably substantially enclosed within automatic injection system 102, and needle guard 104 is held in the proximal position by sleeve bias member 116, if included in the embodiment.

Then, at 810, the user can select the injection site on the recipient, which may be the user or a second person or an animal. If needle 108 is guarded by a removable needle cap, then at 812, the user can remove the needle cap using a needle cap remover insertable into distal end 128 of distal housing 110. The use and operation of needle cap removers is well known in the art. Preferably a cap remover includes a catch configured to catch a needle cap and retain the needle cap upon removal of the cap remover. Next, at 814, distal end 128 is placed in contact with the injection site and, at 816, the user applies pressure distally to keep distal end 128 in contact with the injection site. If proximal housing 112 is configured to include inner and outer proximal housings 402 and 404, the distal pressure is preferably sufficient to move outer housing 404 into the retracted position, thereby allowing the activation of activation system 122. At 818, the user activates activation system 122 in a manner in accordance with the implementation of activation system 122. For instance, in an embodiment activation system 122 is a depressible button, the user depresses button 122 to activate system 102.

The activation of activation system 122 releases driver 304 from the retracted position. Once this occurs, at 820, drive system 302 applies pressure to plunger 109. In an embodiment implementing sleeve 114 and sleeve bias member 116, this pressure causes needle guard 104 and medical cartridge 106 to slide axially along center axis 201 in a distal direction. Then, at 822, needle 108 is exposed from distal end 128 and inserted into the recipient until sleeve 114 reaches the distal limit of movement. In the embodiment where sleeve 114 and sleeve bias member 1.16 are not implemented, needle 108 is already exposed and is inserted into the recipient at 814. Next, at 824, the pressure applied by drive system 302 causes the depression of plunger 109 and the injection of the dose into the recipient. At 826, the depression of plunger 109 engages release mechanism 136 and allows shield 134 to extend distally.

In one embodiment, the pressure applied by shield bias member 138 is greater than the pressure applied by drive system 302. Here, the release of shield 134 causes shield 134 to extend within automatic injection system 102 and withdraws needle 108 from the recipient and into system 102 where needle 108 is substantially covered by shield 134. The extension of shield 134 moves drive system 302 proximally within system 102. Because shield bias member 138 can apply greater pressure than drive system 302, the point at which release mechanism 136 is engaged is preferably set at a point where substantially the entire dose is injected, to prevent the extension of shield 134 before plunger 109 is fully depressed.

In another embodiment, the pressure applied by drive system 302 is greater than the pressure applied by shield bias member 138. Here, though shield 134 is released and free to extend, it is held in the retracted position by the pressure of drive system 302. At 828, the user can detach distal and proximal housings 110 and 112, at which time drive system 302 is no longer in contact with plunger 109 and shield 134 is able to extend to the extended position if not already extended. In one embodiment, the extension of shield 134 raises needle guard 104 and medical cartridge 106 proximally within distal housing 110 such that needle guard 104 is at least partially housed within housing 110. This facilitates the retrieval of guard 104 and cartridge 106 from system 102. Detachment of housings 110 and 112 also allows sleeve 114 to return to the extended position in embodiments where sleeve 114 and sleeve bias member 116 are implemented.

At 830, the user can remove needle guard 108 and medical cartridge 106 from automatic injection system 102. Shield 134 is in the extended position, substantially covering needle 108 and preferably retained, or locked, in the extended position by cooperating catches 140 and 142. The user is free to handle, or dispose of medical cartridge 106 with a reduced risk of inadvertent needle penetration. For instance, with needle guard 104 in place over needle 108, the user is deterred from attempting to reuse medical cartridge 106 either accidentally or purposefully. Also, handling of medical cartridge 106 is also much safer because shield 134 can prevent human skin or tissue from coming into contact with used needle 108. In addition, because needle guard 104 is preferably resistant to dropping and other pressures or impacts, the risk of a accidental damage to medical cartridge 106 is reduced.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions shown in the process flow diagrams described herein is merely illustrative, unless otherwise stated, and the invention can be performed using different or additional process actions, or a different combination or ordering of process actions. As another example, each feature of one embodiment can be mixed and matched with other features shown in other embodiments. Features and processes known to those of ordinary skill may similarly be incorporated as desired. Additionally and obviously, features may be added or subtracted as desired. Accordingly, the invention is not to be restricted except in light of the attached claims and their equivalents.

What is claimed is:

1. A medical injection system, comprising:
   a needle guard, comprising:
   a cartridge housing coupled with a release mechanism and configured to house a pre-filled medical cartridge comprising a needle located on a distal end, a plunger and a carrier configured to carry a dose;
   a shield having an open proximal end and an open distal end, the shield coupled with the cartridge housing and the release mechanism and configured to extend between a retracted and an extended position that substantially covers the needle when the cartridge is housed in the cartridge housing, wherein the release mechanism is configured to maintain the shield in the retracted position and allow the shield to extend upon engagement of the release mechanism; and
   an automatic injection system configured to house the needle guard and the medical cartridge and configured to inject the dose when activated, the automatic injection system comprising:
   a drive system configured to depress the plunger and engage the release mechanism when the automatic injection system is activated; and
   an activation system configured to activate the automatic injection system;
   wherein the needle guard is removable from the automatic injection system with the shield in the extended position after injection of the dose.

2. The system of claim 1, wherein the medical cartridge is insertable into the cartridge housing such that the needle extends from the distal end of the cartridge housing and the plunger extends from the proximal end of the housing and the carrier is housed therebetween.

3. The system of claim 2, further comprising a retainment device at the proximal end of the cartridge housing configured to secure the carrier in the cartridge housing.

4. The system of claim 1, wherein the shield is configured to lock in the extended position.

5. The system of claim 4, wherein the release mechanism is configured to release the shield from the retracted position while the needle is exposed from the distal end of the shield and the plunger is exposed from the proximal end of the shield, and wherein the plunger remains depressible such that substantially the entire dose is injectable upon depression of the plunger.

6. The system of claim 1, further comprising a shield bias member configured to apply pressure to the shield to extend the shield.

7. The system of claim 1, wherein the automatic injection system further comprises:
   a distal housing having an open proximal end and an open distal end, wherein the dose is injected from the distal end of the distal housing; and
   a proximal housing having an open distal end and coupled with the drive system, wherein the proximal end of the distal housing is attachable to the distal end of the proximal housing.

8. The system of claim 7, wherein the distal housing further comprises:
   a sleeve configured to receive the needle guard and slide axially within the automatic injection system; and
   a sleeve bias member configured to apply pressure proximally to the sleeve and to compress upon activation of the automatic injection system prior to depression of the plunger.

9. The system of claim 8, wherein the sleeve comprises a detent that abuts the shield and prevents movement of the needle guard distally within the sleeve.

10. The system of claim 8, wherein the sleeve is configured to receive the needle guard such that the orientation of the needle guard is maintained throughout the range of axial slide motion.

11. The system of claim 8, further comprising a ring coupled with the distal housing and configured to abut the sleeve bias member and wherein the sleeve is slideably coupled with the ring and the ring sets the proximal and distal limits to slide movement of the sleeve.

12. The system of claim 8, wherein the sleeve is configured to encompass a circumference of the needle guard.

13. The system of claim 7, further comprising a depth adjuster coupled with the distal end of the distal housing, wherein the depth adjuster is extendable from the distal end of the distal housing and is substantially fixable in an extended position.

14. The system of claim 1, wherein the drive system comprises:
   a driver releasably coupled with the activation system, axially movable within the automatic injection system between a retracted and an extended position and configured to contact the proximal end of the plunger; and
   a drive bias member configured to apply pressure to the driver, wherein the pressure appliable by the drive bias member is sufficient to depress the plunger and further wherein activation of the activation system releases the driver to allow depression of the plunger.

15. The system of claim 14, wherein the automatic injection system is configured to house the needle guard with the shield in a retracted position and the plunger extended when the driver is in the retracted position.

16. The system of claim 15, wherein the driver is configured to extend and depress the plunger and engage the release mechanism upon activation of the automatic injection system, when the needle guard and medical cartridge are housed within the automatic injection system.

17. The system of claim 14, wherein the automatic injection system is configured to allow the shield to extend to the extended position upon detachment of the proximal and distal housings and after activation of the automatic injection system.

18. The system of claim 14, wherein the pressure appliable by the drive bias member is sufficient to slide the medical cartridge axially towards the distal end of the automatic injection system and insert the needle into a recipient of the dose.

19. The system of claim 14, wherein the drive bias member comprises:
   an inner bias member; and
   an outer bias member having a diameter greater than the inner bias member; and
   a coupling configured to abut a proximal end of the outer bias member and a distal end of the inner bias member and couple the inner bias member with the outer bias member such that the inner and outer bias member can cooperatively extend and compress.

20. The system of claim 14, wherein the activation system comprises a depressible button configured to release the driver when depressed.

21. The system of claim 1, wherein the automatic injection system further comprises an indicator to indicate when the dose is substantially injected.

22. A medical injection system, comprising:
   a needle guard, comprising:
      a cartridge housing coupled with a release mechanism and configured to house a pre-filled medical cartridge comprising a needle located on a distal end, a plunger and a carrier configured to carry a dose;
      a shield having an open proximal end and an open distal end, the shield coupled with the cartridge housing and the release mechanism and configured to extend between a retracted and an extended position that substantially covers the needle when the cartridge is housed in the cartridge housing, wherein the release mechanism is configured to maintain the shield in the retracted position and allow the shield to extend upon engagement of the release mechanism, and wherein the release mechanism comprises a first cooperating catch formed in the shield and a second cooperating catch formed in the cartridge housing, wherein the cooperating catches are configured to engage one another when the shield is in the retracted position and to disengage one another when the release mechanism is engaged when the shield is in the retracted position; and
   an automatic injection system configured to house the needle guard and the medical cartridge and configured to inject the dose when activated, the automatic injection system comprising:
      a drive system configured to depress the plunger and engage the release mechanism when the automatic injection system is activated; and
      an activation system configured to activate the automatic injection system;
   wherein the needle guard is removable from the automatic injection system with the shield in the extended position after injection of the dose.

23. The system of claim 22, wherein the release mechanism further comprises a latch member extending proximally from the proximal end of one of the shield and the cartridge housing, the latch member being deflectable for disengaging the cooperating catches.

24. The system of claim 23, wherein the latch member is deflectable upon depression of the plunger.

* * * * *